(12) United States Patent
Yang et al.

(10) Patent No.: US 10,532,120 B2
(45) Date of Patent: Jan. 14, 2020

(54) SCENT DISPENSER WITH ILLUMINATING ARRANGEMENT

(71) Applicant: Shenzhen Chenbei Technology Co., Ltd., Shenzhen (CN)

(72) Inventors: Lin Yang, Shenzhen (CN); Hai Yang, Shenzhen (CN)

(*) Notice: Subject to any disclaimer, the term of this patent is extended or adjusted under 35 U.S.C. 154(b) by 81 days.

(21) Appl. No.: 15/695,712

(22) Filed: Sep. 5, 2017

(65) Prior Publication Data
US 2019/0070328 A1 Mar. 7, 2019

(51) Int. Cl.
*A61L 9/03* (2006.01)
*F21V 33/00* (2006.01)
*F21Y 115/10* (2016.01)

(52) U.S. Cl.
CPC .......... *A61L 9/032* (2013.01); *F21V 33/0088* (2013.01); *A61L 2209/12* (2013.01); *F21Y 2115/10* (2016.08)

(58) Field of Classification Search
CPC .. A61L 9/032; A61L 2209/12; F21V 33/0088; F21Y 2115/10
See application file for complete search history.

(56) References Cited

U.S. PATENT DOCUMENTS

2017/0119918 A1* 5/2017 Lima ...................... A61L 9/035

* cited by examiner

*Primary Examiner* — Mary Ellen Bowman
(74) *Attorney, Agent, or Firm* — Tsz Lung Yeung (57) ABSTRACT

A scent dispenser includes a main body, a liquid tank unit, a diffusing member for diffusing the liquid from the main body, a control module supported in the main body, an audio speaker unit provided in the main body and electrically connected to the control module, and an illuminating arrangement. The illuminating arrangement includes a supporting frame supported by the main body, and a plurality of illuminating units embedded in the supporting frame and electrically connected to the control module, the illuminating units and the audio speaker unit being driven by the control module to deliver an optimal mix of lighting and sound effect respectively while the liquid is diffused and dispensed from the main body.

17 Claims, 10 Drawing Sheets

FIG.10

SCENT DISPENSER WITH ILLUMINATING ARRANGEMENT

BACKGROUND OF THE PRESENT INVENTION

Field of Invention

The present invention relates to a scent dispenser, and more particularly to a scent dispenser which is capable of delivering an optimal mix of lighting, sound and scent effect to a designated area.

Description of Related Arts

A conventional scent dispenser, such as a conventional oil diffuser, usually delivers diffused oil with specified scent for imparting that scent to a designated area, such as a living room, a bedroom, or even a hotel lobby. However, such conventional diffuser can only deliver a single scent to a designated area. Some sorts of illuminating effects may also be generated by the conventional diffuser. However, the illuminating effect which may be generated by a given diffuser is usually very limited.

As a result, there is a need to improve upon the above-mentioned conventional scent dispenser so that it may deliver an optimal mix of lighting, sound and scent effect to a designated area.

SUMMARY OF THE PRESENT INVENTION

Certain variations of the present invention provide a scent dispenser which is capable of delivering an optimal mix of lighting, sound and scent effect to a designated area.

Certain variations of the present invention provide a scent dispenser which comprises a curved supporting frame upwardly extended from a main body for mounting LED illuminating units thereon and for facilitating enhanced lighting effect of the present invention.

In one aspect of the present invention, it provides a scent dispenser comprising:

a main body;

a liquid tank unit received in the main body for storing a predetermined amount of liquid;

a diffusing member mounted in the main body to communicate with the liquid tank unit for diffusing the liquid from the main body;

a control module supported in the main body;

an audio speaker unit provided in the main body and electrically connected to the control module; and an illuminating arrangement, which comprises:

a supporting frame supported by the main body; and a plurality of illuminating units embedded in the supporting frame and electrically connected to the control module, the illuminating units and the audio speaker unit being driven by the control module to deliver an optimal mix of lighting and sound effect respectively while the liquid is diffused and dispensed from the main body.

This summary presented above is provided merely to introduce certain concepts and not to identify any key or essential features of the claimed subject matter.

DETAILED DESCRIPTION OF THE PREFERRED EMBODIMENT

The following detailed description of the preferred embodiment is the preferred mode of carrying out the invention. The description is not to be taken in any limiting sense. It is presented for the purpose of illustrating the general principles of the present invention.

Referring to FIG. 1 to FIG. 8 of the drawings, a scent dispenser according a preferred embodiment of the present invention is illustrated. Broadly, the scent dispenser may comprise a main body 100, a liquid tank unit 60, a diffusing member 10, a control module 120, an audio speaker unit 27, and an illuminating arrangement 30. The scent dispenser may be utilized to deliver a predetermined of scent to a designated area, such as a living room.

Figure 1:
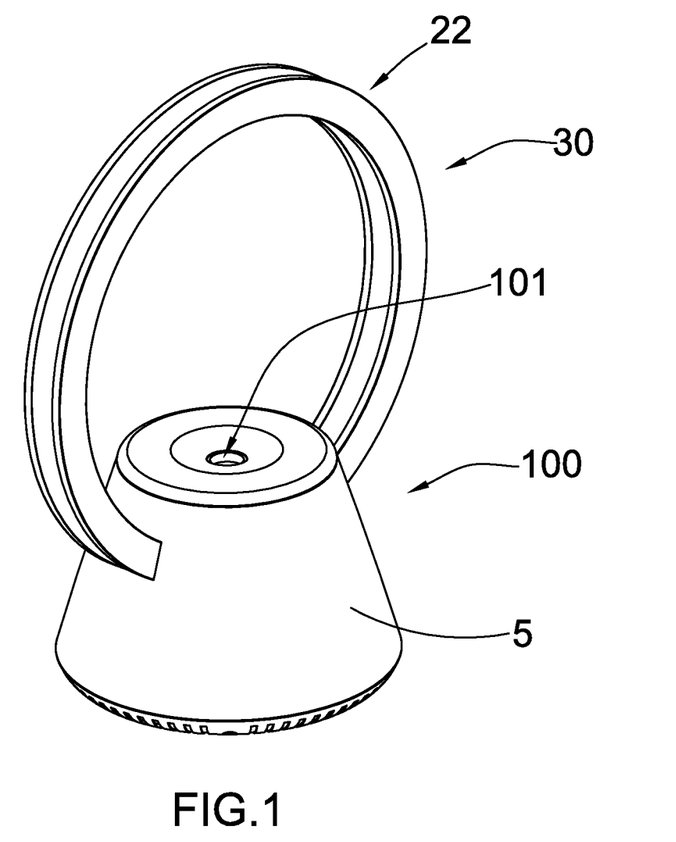
FIG. 1 is a front schematic diagram of a scent dispenser according to a preferred embodiment of the present invention.
Figure 2:
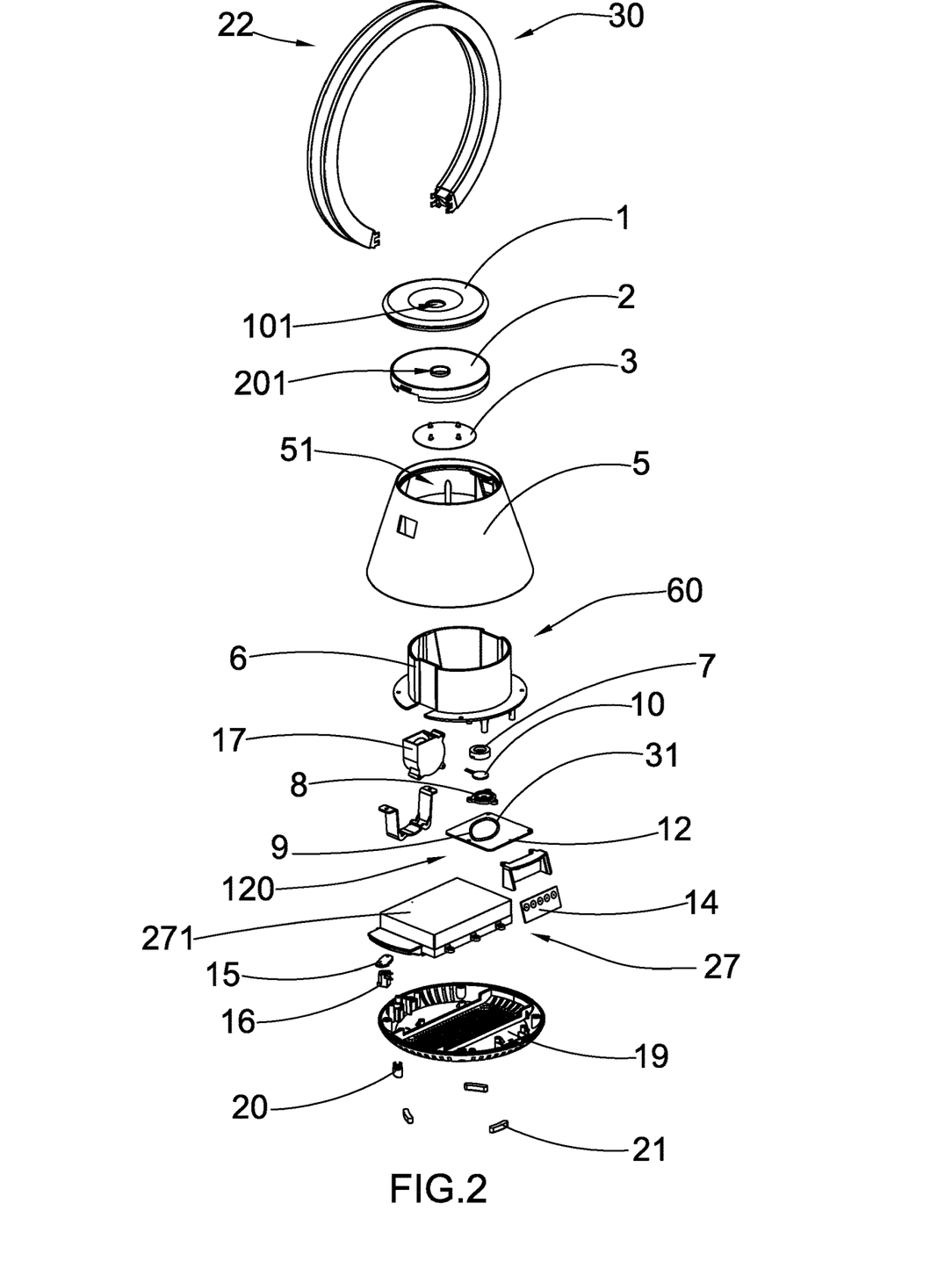
FIG. 2 is an exploded perspective view of the scent dispenser according to the preferred embodiment of the present invention.

The liquid tank unit 60 may be received in the main body 100 for storing a predetermined amount of liquid, such as oil, water, or other solutions. The diffusing member 10 may be mounted in the main body 100 to communicate with the liquid tank unit 60 for vaporizing the liquid from the main body 100. The control module 120 may be supported in the main body 100. Moreover, the audio speaker unit 27 may be provided in the main body 100 and electrically connected to the control module 120.

Figure 3:
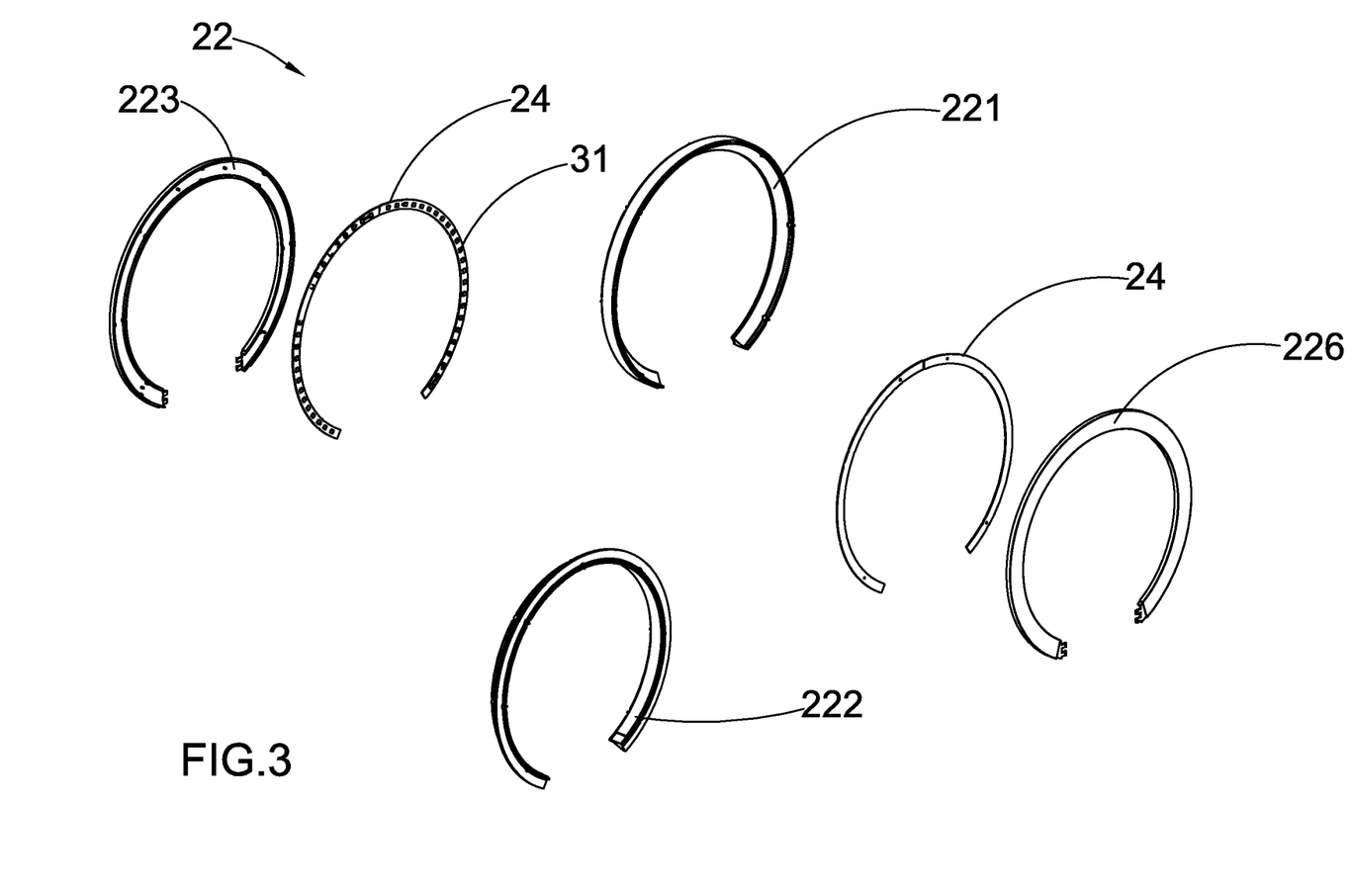
FIG. 3 is an exploded perspective view of an illuminating arrangement of the scent dispenser according to the preferred embodiment of the present invention.

The illuminating arrangement 30 may comprise a supporting frame 22 supported by the main body 100, and a plurality of illuminating unit 31.

The plurality of illuminating units 31 may be embedded in the supporting frame 22 and electrically connected to the control module 120. The illuminating units 31 and the audio speaker unit 27 may be driven by the control module 120 to deliver an optimal mix of lighting and sound effect respectively while the liquid is diffused and dispensed from the main body 100.

According to the preferred embodiment of the present invention, the main body 100 may comprise a main housing 5 having a receiving cavity 51, a top cover 1 provided on top of the main housing 5, and a base member 19 mounted on a bottom portion of the main housing 5. The main housing 5 may have a substantially circular cross-sectional shape and may be tapered in structure. Thus, a cross-sectional diameter of main housing 5 may be gradually increasing from the top to the bottom thereof. The receiving cavity 51 may be formed as a space surrounded by the main housing 5, the top cover 1, and the base member 19. The top cover 1 may have a through hole 101 formed thereon.

Figure 4:
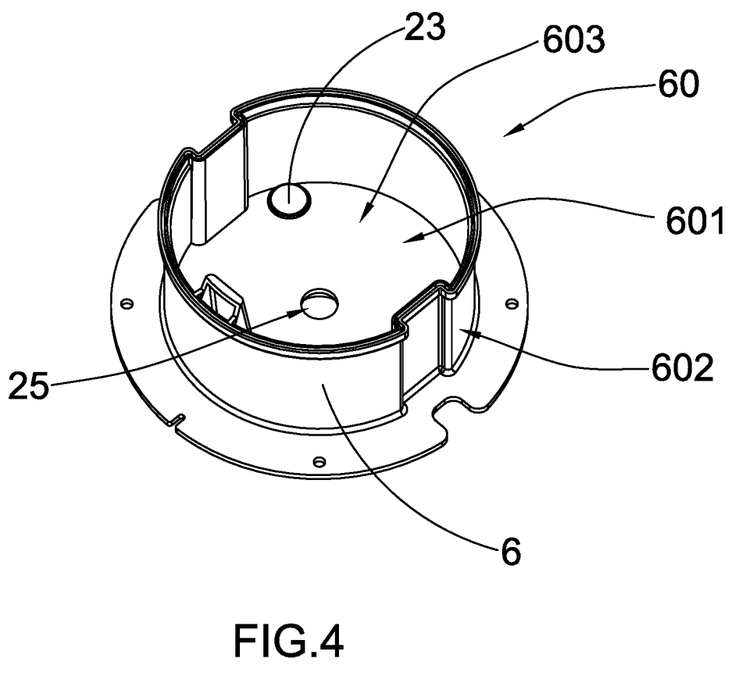
FIG. 4 is a perspective view of a liquid tank of the scent dispenser according to the preferred embodiment of the present invention.

The liquid tank unit 60 may comprise a liquid tank 6 and a tank cover 2 provided on top of the liquid tank 6. The liquid tank 6 may be detachably mounted in the main housing 5 and may be adapted for storing a certain amount of scent-producing liquid such as oil, or simply water. The tank cover 2 may have a tank hole 201 formed thereon. The tank hole 201 may align with the through hole 101 of the top cover. As shown in FIG. 4 of the drawings, the liquid tank 6 may have a bottom wall 601, a peripheral sidewall 602 extended from the bottom wall 601, and a storage cavity 603 formed as a space surrounded by the bottom wall 601 and the peripheral sidewall 602. The liquid tank 6 may further have a securing hole 25 formed at a bottom wall 601 thereof. The diffusing member 10 may be accommodated in the securing hole 25 through a securing member 8. A sealing ring 7 may be provided in the securing hole 25 for preventing liquid from leaking out of the storage cavity 603 through the securing hole 25. The securing member 8 may act as a cover to cover the diffusing member 10, the sealing ring 7, and the securing hole 25 from the bottom of the liquid tank 6, as shown in FIG. 2 of the drawings.

In this preferred embodiment, the diffusing member 10 may be act as a heat plate to heat up the liquid stored in the liquid tank 6. When the liquid in the liquid tank 6 is heated up, vaporization may occur and vapor may escape out of the liquid tank 6 through the tank hole 201.

The liquid tank 6 may further comprise a liquid level sensor 23 formed on the bottom wall 601 and in the storage cavity 603 for detecting the liquid level in the storage cavity 603. The liquid level sensor 23 may be arranged to send a signal to the control module 120 when the liquid level in the liquid tank 6 is below a predetermined threshold.

The control module 120 may comprise a main Printed Circuit Board (PCB) 12 detachably mounted in the main housing 5 at a position below the liquid tank 6. The main PCB 12 may comprise a microcontroller 126 electrically connected to the diffusing member 10, the illuminating arrangement 30 and the audio speaker unit 27 for controlling and coordinating an operation of each of these components.

The supporting frame 22 of the illuminating arrangement 30 may be mounted on the main housing 5 and upwardly extended therefrom. As shown in FIG. 1 of the drawings, the supporting frame 22 may have a substantially ring-shaped or curved-shaped cross section having two ends mounted on two sides of the main housing 5 respectively. The illuminating units 31 may be provided on the supporting frame 22 for providing predetermined illuminating effect for the scent dispenser.

Figure 5:
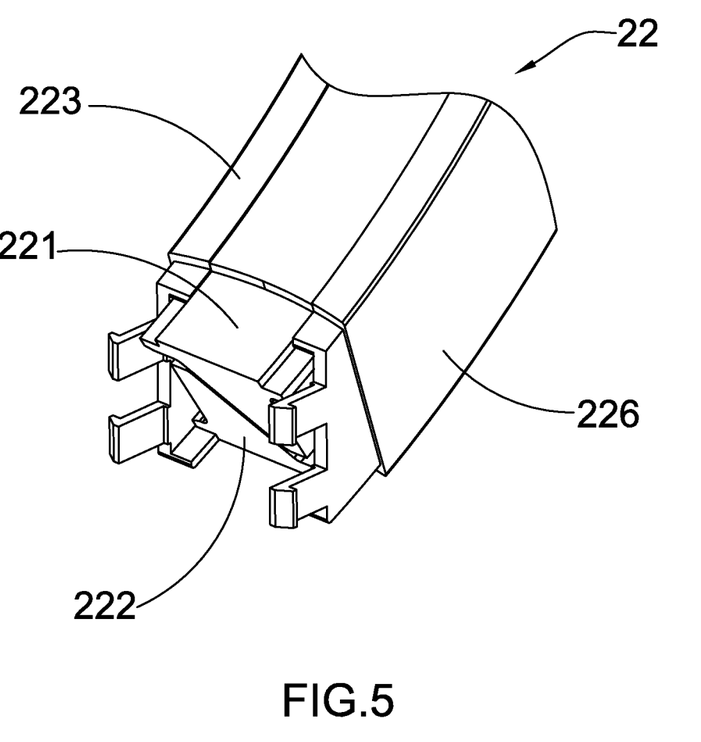
FIG. 5 is a schematic diagram of a supporting frame of the illuminating arrangement of the scent dispenser according to the preferred embodiment of the present invention.

The supporting frame 22 may comprise a front frame cover 223, a rear frame cover 226, an upper frame cover 221, and a bottom frame cover 222. As shown in FIG. 5 of the drawings, the front frame cover 223 and the rear frame cover 226 may be connected in a side-by-side manner to accommodate the upper frame cover 221 and the bottom frame cover 222 respectively.

Each of the upper frame cover 221 and the bottom frame cover 222 may have a substantially triangular cross-sectional shape in which an inclined surface of the upper frame cover 221 may be arranged to bias against a corresponding inclined surface of the bottom frame cover 222. A light-inadmissible coating may be formed on the inclined surfaces of the upper frame cover 221 and the bottom frame cover 222 to prevent light from passing from the upper frame cover 221 to the bottom frame cover 222, or vice versa.

The illuminating arrangement 30 may further comprise a plurality of mounting circuit boards 224 wherein the illuminating units 31 are mounted on the mounting circuit board 224 to form a line source of illumination. Each of the mounting circuit boards 224 may act as a physical and electrical carrier for supporting all illuminating units 31. Each of the mounting circuit boards 224 may be configured to be electrically conductive so that the illuminating units 31 may connected in a predetermined electrical connection on the corresponding mounting circuit board 224. Each of the illuminating units 31 may be configured as a Light Emitting Diode (LED) for generating illumination.

Figure 6:
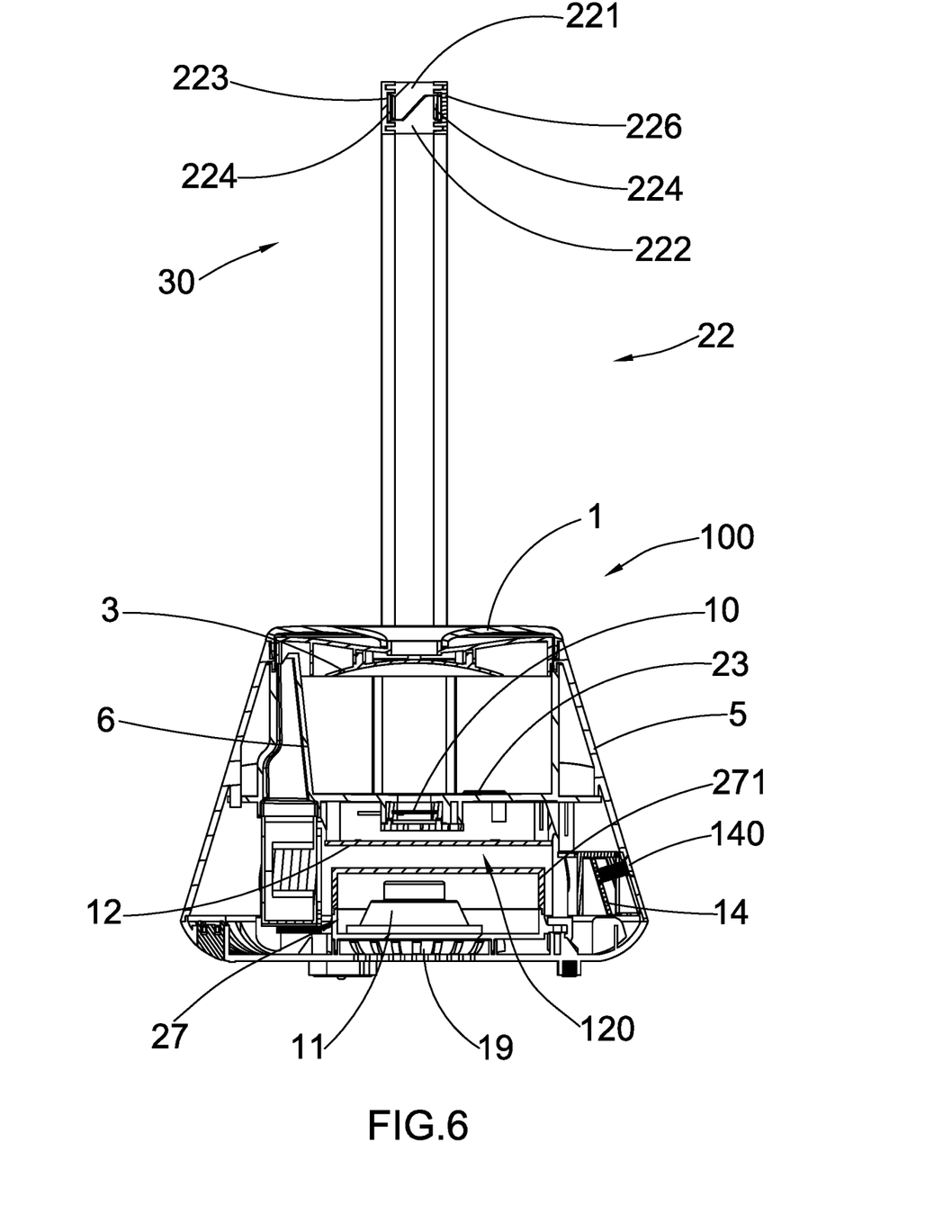
FIG. 6 is a schematic side view of the scent dispenser according to the preferred embodiment of the present invention.

As shown in FIG. 6 of the drawings, the mounting circuit boards 224 are mounted on inner surfaces of the front frame cover 223 and the rear frame cover 226 respectively. Each of the mounting circuit boards 224 may carry a predetermined number of illuminating units 31 for generating illumination. In the preferred embodiment of the present invention, the main housing 5, the base member 19, the front frame cover 223 and the rear frame cover 226 may be configured or made from a material which is light inadmissible. On the other hand, the upper frame cover 221, the bottom frame cover 222, the liquid tank 6, the tank cover 2, and the top cover 1 may be configured or made from a material which is light admissible. Exemplary light admissible materials may include polyoxymethylene (POM), polyamide (PA), high-impact polystyrene (HIPS), polyphenylene oxide (PPO) etc. Exemplary light inadmissible materials may include Polyvinyl chloride (PVC), polyethylene (PE), polypropylene (PP) etc. With the use of various light admissible and light inadmissible material, and with the help of main PCB 12, different lighting effects may be generated by the scent dispenser of the present invention.

The illuminating arrangement 30 may further comprise a LED illuminating module 9 mounted in the main housing 5 at a position below the liquid tank 6 for acting as a second light source to deliver illumination from the main housing 5. The LED illuminating module 9 may comprise at least one illuminating unit 31 for generating illumination. This illuminating unit 31 may be configured as LED. The LED illuminating module 9 may have a ring-shape structure and may be incorporated on the main PCB 12, as shown in FIG. 2 of the drawings.

The scent dispenser may further comprise a blocking member 3 provided between the tank cover 2 and the liquid tank 6 for facilitating effective diffusion or vaporization of the liquid stored in the liquid tank 6. Specifically, the blocking member 3 may have a substantially circular cross section and may have a diameter less than that of the tank cover 2 but larger than that of the tank hole 201, so that a certain amount of vaporized liquid may be trapped or blocked by the blocking member 3 as liquid droplets. This mechanism may help vaporization of the liquid to be more effective and efficient. The blocking member 3 may be configured from a material which is light admissible. Exemplary light admissible materials have been described above.

Figure 7:
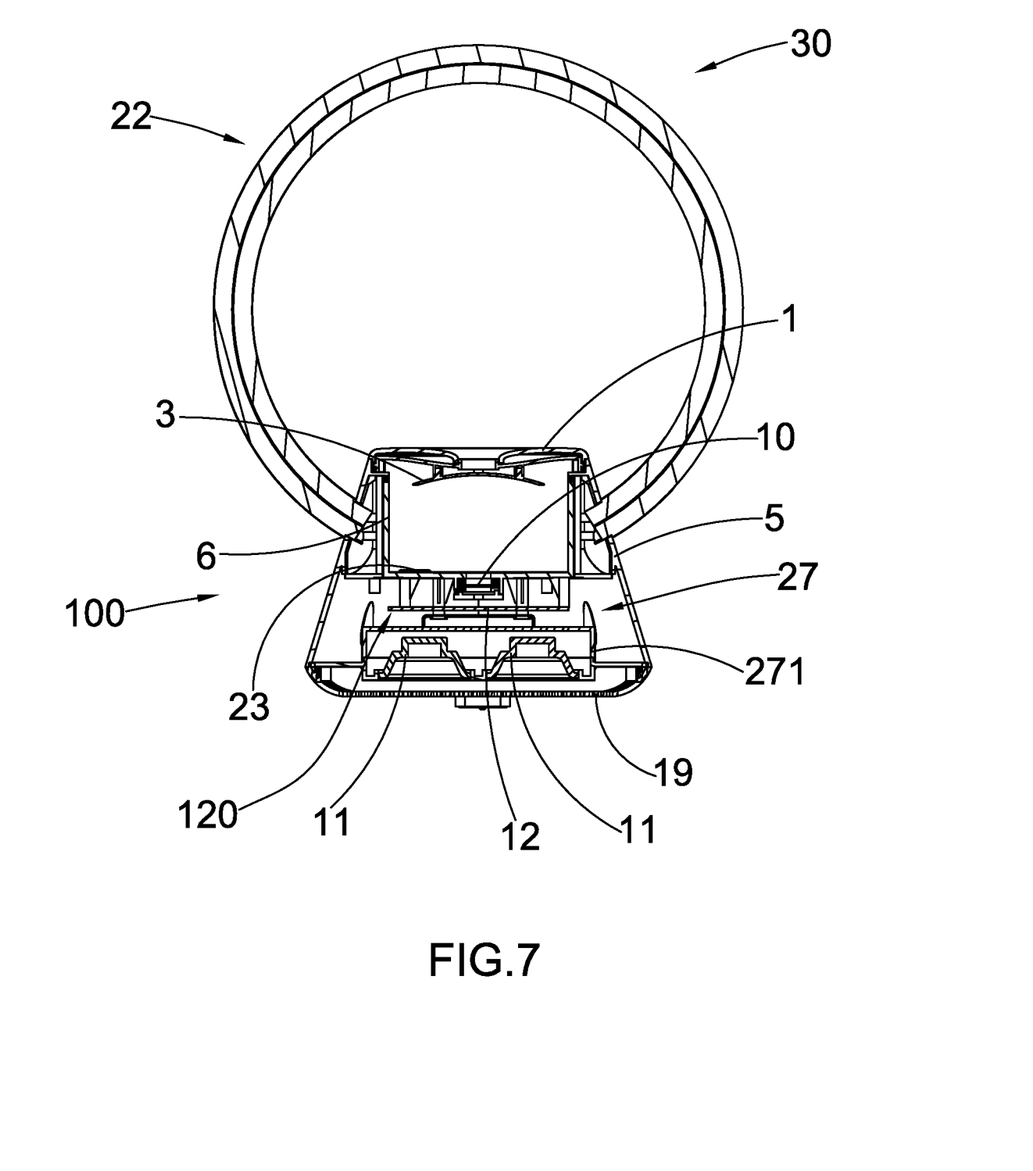
FIG. 7 is a schematic front view of the scent dispenser according to the preferred embodiment of the present invention.

The audio speaker unit 27 may comprise a speaker housing 271, and a plurality of (but at least one) audio speakers 11 accommodated in the speaker housing 271. The speaker housing 271 may be provided and protected in the main housing 5. As shown in FIG. 6 and FIG. 7 of the drawings, the speaker housing 271 may be mounted at a bottom portion of the main housing 5. The audio speakers 11 may deliver audible sound. The audio speakers 11 may be electrically connected and controlled by the main PCB 12 for delivering the most optimal audible sound which may optimally blend with the lighting effect and the scent generated by the diffusing member 10.

The control module 120 may further comprise a control PCB 14 mounted in the main housing 5 and electrically connected to the main PCB 12, and a control panel 140 electrically connected to the control PCB 14 and provided on an exterior surface of the main body 100, wherein a user may be able to control the operation of the scent dispenser through operating on the control panel 140.

Figure 8:
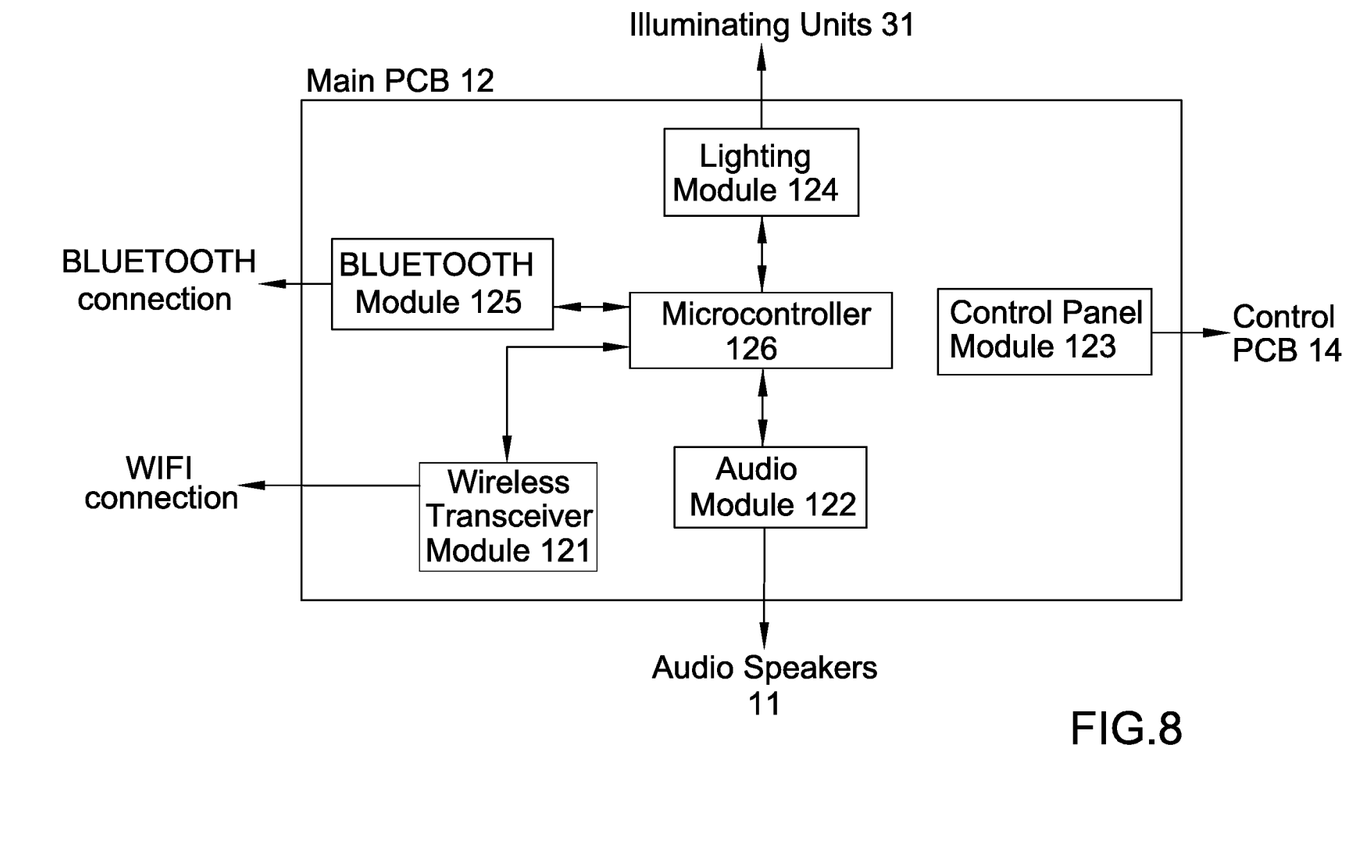
FIG. 8 is a schematic diagram of a main Printed Circuit Board according to the preferred embodiment of the present invention.

As shown in FIG. 8 of the drawings, the main PCB 12 may have a wireless transceiver module 121, an audio module 122, a control panel module 123, a lighting module 124, and a short-range wireless communication module 125 for controlling the WIFI connection, the audio speaker 11, the control PCB 14, the illuminating arrangement 30, and BLUETOOTH connection respectively. The wireless transceiver module 121 may be arranged to connect to a mobile device (such as a smartphone) through WiFi connection. A WIFI connection button 20 may be provided on the base member 19 for activating wireless transceiver module 121. The audio module 122 may be electrically connected to the audio speaker 11 and may control an operation thereof. The control panel module 123 may be arranged to receive and process control signals received from the control PCB 14. The lighting module 124 may control an operation of the illuminating arrangement 30 in response to the signals received from the control panel 140 or from the mobile device connected through the wireless transceiver module 121 or the short-range wireless communication module 125. The short-range wireless communication module 125 may be configured to connect to the mobile device (such as the smartphone) through BLUETOOTH connectivity standards (i.e. a short-range wireless communication protocol for phones, computers, or other electronic devices).

Furthermore, the scent dispenser may further comprise an electric socket 16 and a socket holder 15 provided on the main body 100 for acquiring power from an external power source such as a AC/DC power source. The electric socket 16 may be electrically connected to the main PCB 12. A fan 17 may be provided within the main body 100 for distributing diffused liquid to an exterior of the main body 100. A plurality of supporting stands 21 may be provided underneath the base member 19.

The operation of the present invention is as follows: a user may be able to control the operation of the present invention by pressing buttons on the control panel 140, or by operating on the mobile device which is connected to the scent dispenser through the short-range wireless communication module 125 or the wireless transceiver module 121. Moreover, the main PCB 12 may be programmed to have a selection of different mix of illuminating effects and audio music so that a user may be able to select the most optimal set of scent, lighting effect and audible sound.

Figure 9:
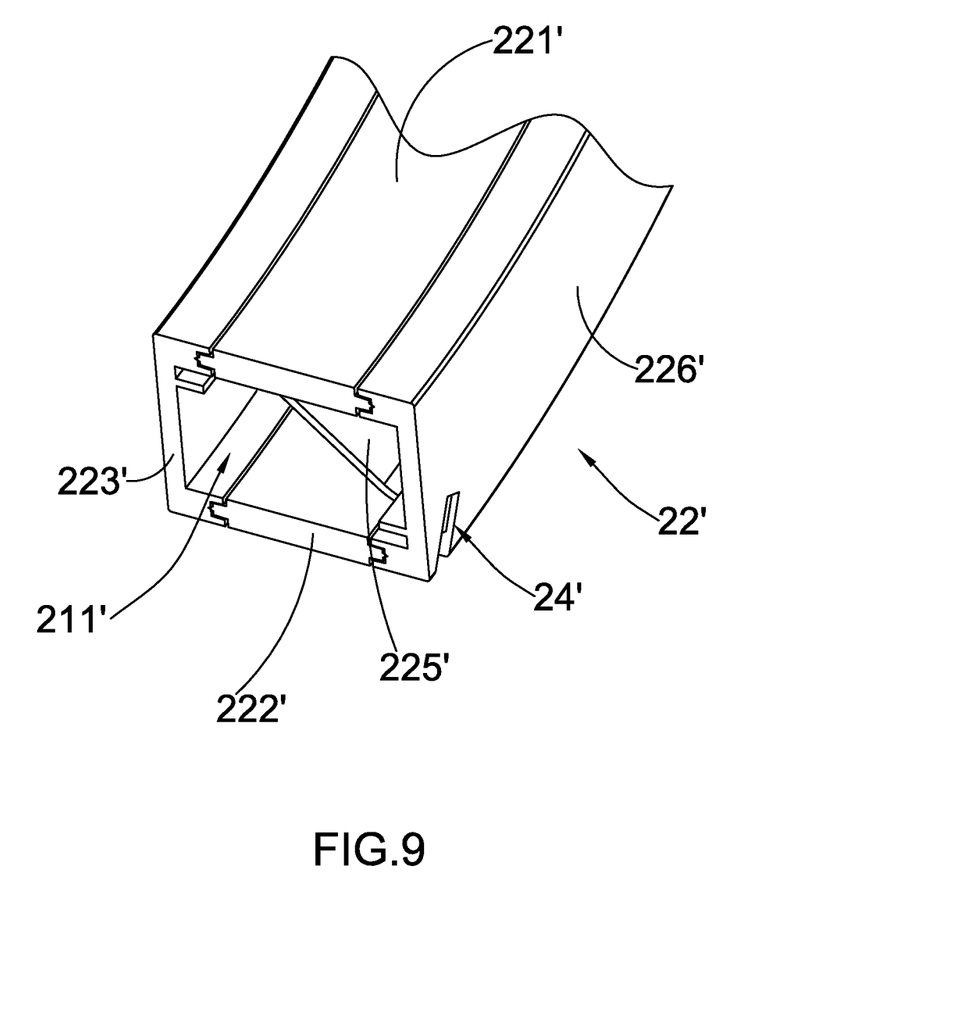
FIG. 9 is an alternative mode of the scent dispenser according to the preferred embodiment of the present invention.
Figure 10:
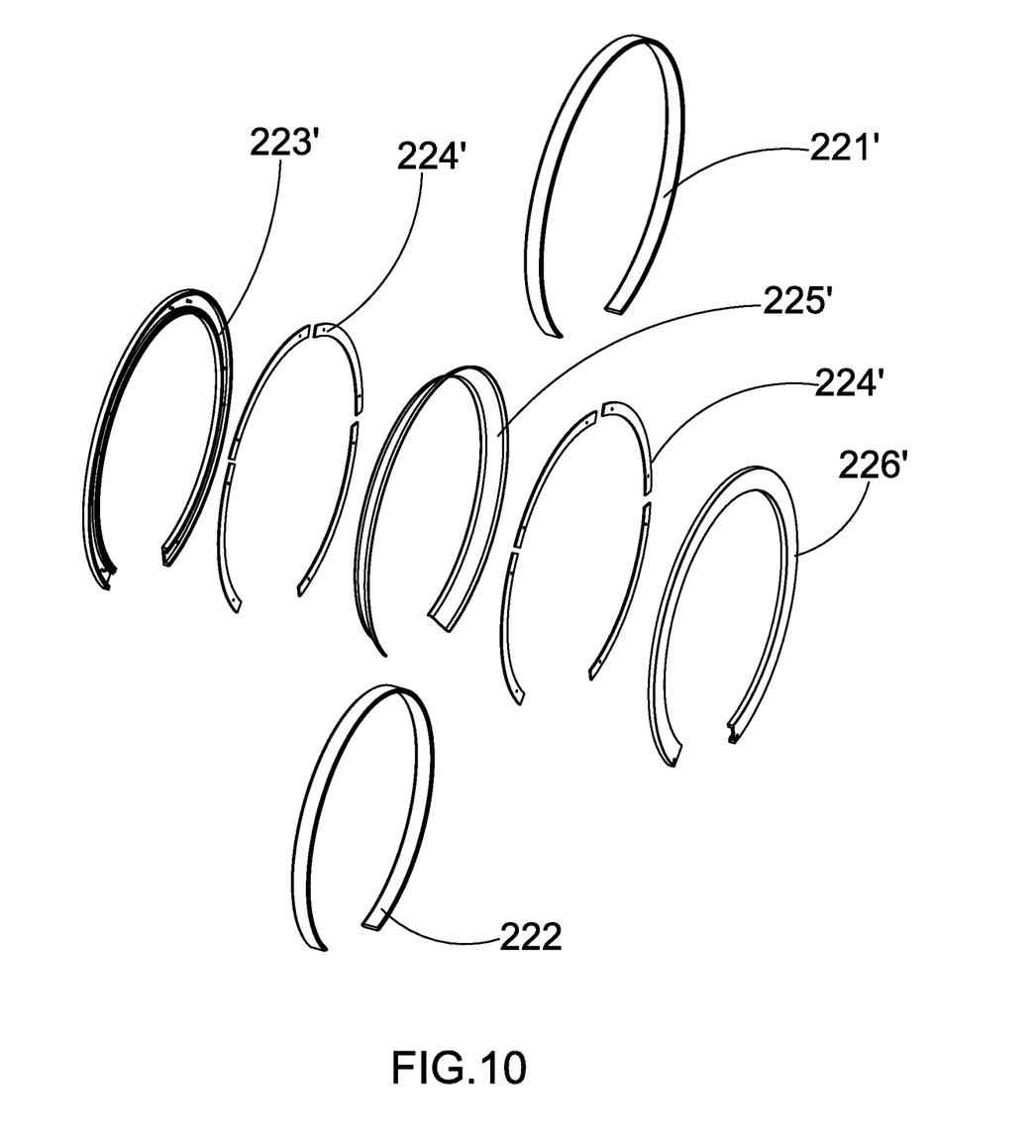
FIG. 10 is an exploded perspective view of an illuminating arrangement of the scent dispenser according to the alternative mode of the preferred embodiment of the present invention.

Referring to FIG. 9 to FIG. 10 of the drawings, an alternative mode of the scent dispenser according to the preferred embodiment of the present invention is illustrated. The alternative mode is similar to the preferred embodiment, except the supporting frame 22' of the illuminating arrangement 30. According to the alternative mode, the supporting frame 22' may comprise a front frame cover 223', a rear frame cover 226', an upper frame cover 221', a bottom frame cover 222', and a partitioning member 225'. An illuminating space 211' is formed as a space surrounded by the front frame cover 223', the rear frame cover 226', the upper frame cover 221', and the bottom framer cover 222'. As shown in FIG. 9 of the drawings, the front frame cover 223' and the rear frame cover 226' may be connected between two sides of the upper frame cover 221' and the bottom frame cover 222' respectively.

The partitioning member 225' may be inclinedly disposed in the illuminating space 211' formed between the front frame cover 223', the rear frame cover 226', the upper frame cover 221' and the bottom frame cover 222'. The partitioning member 225' may extend along a diagonal of the illuminating space 211'. The mounting circuit boards 224' may be attached on the inner surfaces of the front frame cover 223' and the rear frame cover 226' respectively. The partitioning member 225' may optically separate the mounting circuit boards 224' and the illuminating units 31' attached on the respective mounting circuit board 224'.

The mounting circuit boards 224' may be mounted on an inner side surface of the front frame cover 223' and the rear frame cover 226'.

In this alternative mode, the main housing 5', the base member 19', the front frame cover 223', the rear frame cover 226' and the partitioning member 225' may be configured or made from a material which is light inadmissible. On the other hand, the upper frame cover 221', the bottom frame cover 222', the liquid tank 6, the tank cover 2, and the top cover 1 may be configured or made from a material which is light admissible. Exemplary light admissible materials and light inadmissible materials have been described above.

Moreover, each of the front frame cover 223' and the rear frame cover 226' may have an engagement slot 24' for engaging with the main housing 5' so as to detachably engage the supporting frame 22' on the main housing 5'.

The present invention, while illustrated and described in terms of a preferred embodiment and several alternatives, is not limited to the particular description contained in this specification. Additional alternative or equivalent components could also be used to practice the present invention.

What is claimed is:

1. A scent dispenser, comprising:
a main body which comprises a main housing having a receiving cavity, a top cover having a through hole and provided on top of said main housing, and a base member mounted on a bottom portion of said main housing;
a liquid tank unit received in said main body for storing a predetermined amount of liquid;
a diffusing member mounted in said main body to communicate with said liquid tank unit for diffusing said liquid from said main body;
a control module supported in said main body;
an audio speaker unit provided in said main body and electrically connected to said control module; and
an illuminating arrangement, which comprises:
a supporting frame upwardly extended from said main housing and comprising a front frame cover, a rear frame cover, an upper frame cover, and a bottom frame cover, said front frame cover and said rear frame cover being connected in a side-by-side manner to accommodate said upper frame cover and said bottom frame cover respectively; and
a plurality of illuminating units embedded in said supporting frame and electrically connected to said control module, said illuminating units and said audio speaker unit being driven by said control module to deliver an optimal mix of lighting and sound effect respectively while said liquid is diffused and dispensed from said main body.

2. The scent dispenser, as recited in claim 1, wherein said liquid tank unit comprises a liquid tank and a tank cover provided on top of said liquid tank, said liquid tank being detachably mounted in said main housing and adapted for storing a certain amount of scent-producing liquid, said tank cover having a through tank hole which aligns with said through hole of said top cover.

3. The scent dispenser, as recited in claim 2, wherein said liquid tank has a bottom wall, a peripheral sidewall extended from said bottom wall, and a storage cavity formed as a space surrounded by said bottom wall and said peripheral sidewall, said liquid tank further having a securing hole formed at a bottom wall thereof, said diffusing member being accommodated in said securing hole.

4. The scent dispenser, as recited in claim 3, wherein said control module comprises a main PCB detachably mounted in said main housing at a position below said liquid tank, said main PCB comprises a microcontroller electrically connected to said diffusing member, said illuminating arrangement and said audio speaker unit for controlling and coordinating an operation of each of said diffusing member, said illuminating arrangement and said audio speaker unit.

5. The scent dispenser, as recited in claim 4, wherein said supporting frame has a substantially ring-shaped cross section having two ends mounted on two sides of said main housing respectively, said illuminating units may being provided on said supporting frame for providing illuminating effect.

6. The scent dispenser, as recited in claim 4, wherein each of said upper frame cover and said bottom frame cover has a substantially triangular cross-sectional shape in which an inclined surface of said upper frame cover is arranged to bias against a corresponding inclined surface of said bottom frame cover, each of said inclined surfaces of said upper frame cover and said bottom frame cover being coated with a light-inadmissible coating.

7. The scent dispenser, as recited in claim 5, wherein each of said upper frame cover and said bottom frame cover has a substantially triangular cross-sectional shape in which an inclined surface of said upper frame cover is arranged to bias against a corresponding inclined surface of said bottom frame cover, each of said inclined surfaces of said upper frame cover and said bottom frame cover being coated with a light-inadmissible coating.

8. The scent dispenser, as recited in claim 6, wherein said illuminating arrangement further comprises a plurality of mounting circuit boards wherein said illuminating units are mounted on said mounting circuit board to form a line source of illumination.

9. The scent dispenser, as recited in claim 7, wherein said illuminating arrangement further comprises a plurality of mounting circuit boards wherein said illuminating units are mounted on said mounting circuit board to form a line source of illumination.

10. The scent dispenser, as recited in claim 8, wherein said mounting circuit boards are mounted on inner surfaces of said front frame cover and said rear frame cover respectively.

11. The scent dispenser, as recited in claim 9, wherein said mounting circuit boards are mounted on inner surfaces of said front frame cover and said rear frame cover respectively.

12. The scent dispenser, as recited in claim 11, wherein said main housing, said base member, said front frame cover and said rear frame cover are made from a material which is light inadmissible, said upper frame cover, said bottom frame cover, said liquid tank, said tank cover, and said top cover being made of a material which is light admissible.

13. The scent dispenser, as recited in claim 12, wherein said illuminating arrangement further comprises a LED illuminating module incorporated on said main PCB for acting as a second light source to deliver illumination from said main housing, said LED illuminating module comprising at least one illuminating unit for generating illumination, and having a ring-shape structure.

14. The scent dispenser, as recited in claim 13, wherein said main PCB comprises a wireless transceiver module, and a short-range wireless communication module for controlling WIFI connection and short-range wireless connection respectively.

15. A scent dispenser, comprising:
a main body which comprises a main housing having a receiving cavity, a top cover having a through hole and provided on top of said main housing, and a base member mounted on a bottom portion of said main housing;
a liquid tank unit received in said main body for storing a predetermined amount of liquid;
a diffusing member mounted in said main body to communicate with said liquid tank unit for diffusing said liquid from said main body;
a control module supported in said main body;
an audio speaker unit provided in said main body and electrically connected to said control module; and
an illuminating arrangement, which comprises:
a supporting frame which upwardly extends from said main housing and comprises a front frame cover, a rear frame cover, an upper frame cover, a bottom frame cover, and a partitioning member, and an illuminating space formed as a space surrounded by said front frame cover, said rear frame cover, said upper frame cover, and said bottom framer cover, said front frame cover and said rear frame cover being connected between two sides of said upper frame cover and said bottom frame cover respectively, said partitioning member being inclinedly disposed in said illuminating space, and extending along a diagonal of said illuminating space; and
a plurality of illuminating units embedded in said supporting frame and electrically connected to said control module, said illuminating units and said audio speaker unit being driven by said control module to deliver an optimal mix of lighting and sound effect respectively while said liquid is diffused and dispensed from said main body.

16. The scent dispenser, as recited in claim 15, wherein said main housing, said base member, said front frame cover, said rear frame cover and said partitioning member being made from a material which is light inadmissible, said upper frame cover, said bottom frame cover, said liquid tank, said tank cover, and said top cover being made from a material which is light admissible.

17. The scent dispenser, as recited in claim 16, wherein said illuminating arrangement further comprises a plurality of mounting circuit boards wherein said illuminating units are mounted on said mounting circuit board to form a line source of illumination, said mounting circuit boards being mounted on inner surfaces of said front frame cover and said rear frame cover respectively.

* * * * *